(12) United States Patent (10) Patent No.: US 9,770,714 B2
Hamasaki et al. (45) Date of Patent: Sep. 26, 2017

(54) ANALYSIS PACKAGE FOR DETECTING PARTICLES IN A SAMPLE LIQUID, AND INCLUDING SHIELD LAYERS

(71) Applicant: KABUSHIKI KAISHA TOSHIBA, Minato-ku, Tokyo (JP)

(72) Inventors: Hiroshi Hamasaki, Hiratsuka Kanagawa (JP); Michihiko Nishigaki, Kawasaki Kanagawa (JP); Yutaka Onozuka, Yokohama Kanagawa (JP); Kentaro Kobayashi, Tokyo (JP); Hiroko Miki, Kawasaki Kanagawa (JP); Naofumi Nakamura, Tokyo (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 59 days.

(21) Appl. No.: 14/848,312

(22) Filed: Sep. 8, 2015

(65) Prior Publication Data

US 2016/0231263 A1 Aug. 11, 2016

(30) Foreign Application Priority Data

Feb. 9, 2015 (JP) ................................. 2015-023114

(51) Int. Cl.
 *B01L 3/00* (2006.01)
 *G01N 33/487* (2006.01)
(52) U.S. Cl.
 CPC ..... *B01L 3/5027* (2013.01); *B01L 2200/0647* (2013.01); *B01L 2300/0645* (2013.01); *B01L 2300/0681* (2013.01); *B01L 2300/0816* (2013.01); *B01L 2300/0887* (2013.01); *B01L 2400/0421* (2013.01); *B01L 2400/086* (2013.01); *G01N 33/4875* (2013.01)

(58) Field of Classification Search
 CPC ........................... B01L 3/502715; G01N 27/00
 USPC .................................................. 324/464–470
 See application file for complete search history.

(56) References Cited

U.S. PATENT DOCUMENTS

| | | | |
|---|---|---|---|
| 2004/0144658 A1 | 7/2004 | Flory | |
| 2004/0248306 A1* | 12/2004 | Hernandez | B01L 3/5027 436/39 |
| 2006/0093517 A1* | 5/2006 | Yokoyama | B01L 3/502715 422/400 |
| 2008/0311375 A1 | 12/2008 | Harnack et al. | |

(Continued)

FOREIGN PATENT DOCUMENTS

| | | |
|---|---|---|
| JP | 2016024013 | 2/2016 |
| WO | 2016009674 A1 | 1/2016 |

*Primary Examiner* — Jeff Natalini
(74) *Attorney, Agent, or Firm* — Holtz, Holtz & Volek PC

(57) ABSTRACT

According to one embodiment, an analysis package including a board including an electrical terminal, an analysis chip provided at the board, the chip including a detector for detecting a particle, a flow channel of a sample liquid for particle detection to the detector, and a liquid receiver for introducing the sample liquid into the flow channel, a mold provided to cover the board on which the analysis chip is provided, the mold comprising an opening above the liquid receiver, a first shield layer provided on a back surface of the board, and a second shield layer provided to be attachable and detachable on an opposite side to the analysis chip of the mold, the second shield layer being electrically connected to a part of the electrical terminal.

16 Claims, 6 Drawing Sheets

(56) References Cited

U.S. PATENT DOCUMENTS

| | | | |
|---|---|---|---|
| 2012/0100478 A1* | 4/2012 | Sukeno | G03G 9/0806 |
| | | | 430/109.4 |
| 2014/0083859 A1* | 3/2014 | Baeumner | B81B 1/006 |
| | | | 204/601 |
| 2014/0320849 A1* | 10/2014 | Chou | B03C 5/026 |
| | | | 356/72 |
| 2015/0004627 A1* | 1/2015 | Wu | G01N 27/02 |
| | | | 435/7.8 |
| 2015/0082888 A1* | 3/2015 | Otsu | G01N 29/12 |
| | | | 73/587 |

* cited by examiner

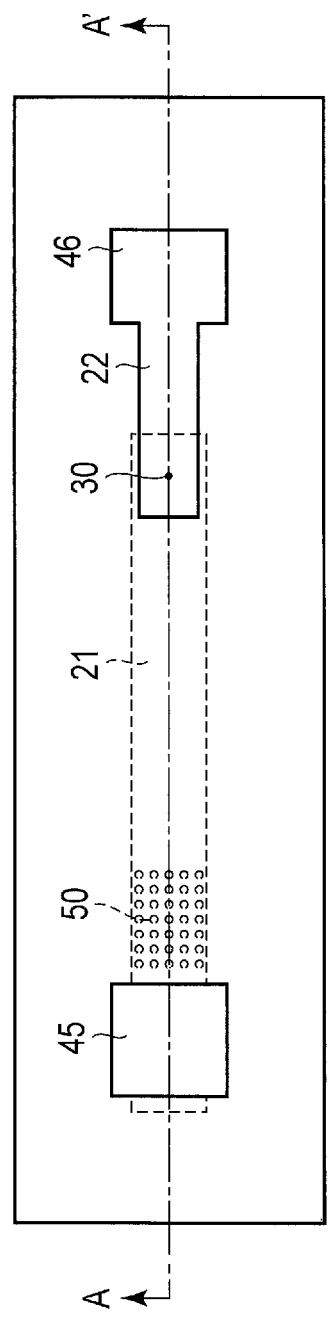
F I G. 6A
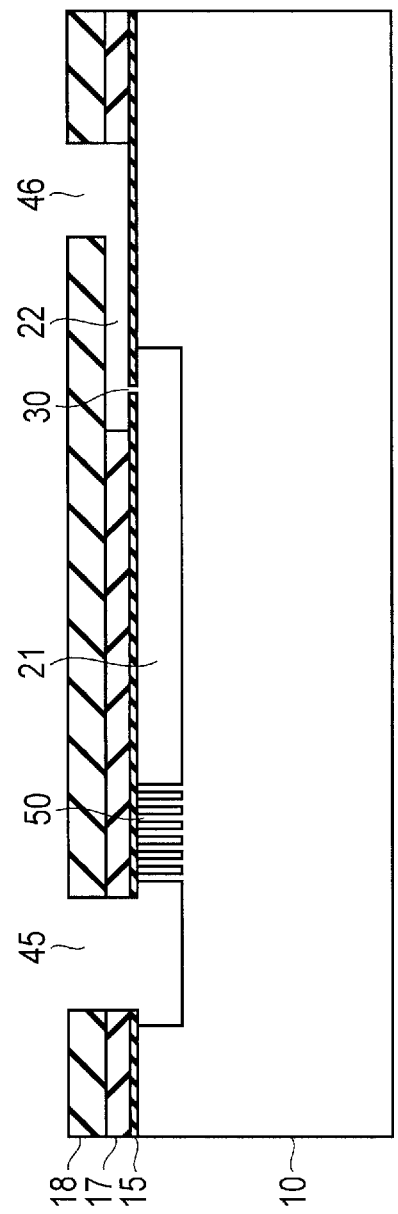
F I G. 6B

… (1)

ANALYSIS PACKAGE FOR DETECTING PARTICLES IN A SAMPLE LIQUID, AND INCLUDING SHIELD LAYERS

CROSS-REFERENCE TO RELATED APPLICATIONS

This application is based upon and claims the benefit of priority from Japanese Patent Application No. 2015-023114, filed Feb. 9, 2015, the entire contents of which are incorporated herein by reference.

FIELD

Embodiments described herein relate generally to an analysis package for detecting particles in a sample liquid.

BACKGROUND

In recent years, a microanalysis chip on which microfluidic devices such as microflow channels and detection mechanisms are integrated has been attracting attention in the field of biotechnology and healthcare. In this kind of chip, particles and biopolymers included in a sample liquid can be detected by letting the sample liquid flow in a flow channel and acquiring the displacement of the particles, etc., in the sample liquid as an electrical signal by the variation of electrical resistance.

BRIEF DESCRIPTION OF THE DRAWINGS

FIG. 6A is a plan view showing an example of a semiconductor microanalysis chip used in the first and second embodiments;

FIG. 6B is a cross-sectional view taken along line A-A' of FIG. 6A;

DETAILED DESCRIPTION

In general, according to one embodiment, an analysis package comprises: a board comprising an electrical input/output terminal; an analysis chip provided at a part of the board, the chip comprising a detector for detecting a particle, a flow channel for injecting and ejecting a sample liquid for particle detection to the detector, and a liquid receiver for introducing the sample liquid into the flow channel; a mold provided to cover the board on which the analysis chip is provided, the mold comprising an opening above the liquid receiver; a first shield layer provided on a back surface of the board; and a second shield layer provided to be attachable and detachable on an opposite side to the analysis chip of the mold, the second shield layer being electrically connected to a part of the electrical input/output terminal.

Analysis packages of embodiments, for instance, microanalysis packages will be described hereinafter with reference to the accompanying drawings.

(First Embodiment)

A microanalysis chip has weak strength, and thus, needs to be packaged in a resin mold, etc., when being actually used as a product. At this time, a sample liquid needs to be dropped into a reservoir of a microflow channel from an opening provided in a package. On the other hand, because a particle detection signal is weak, the package needs to be shielded to remove the influence of electrical noise. However, even if a shield is provided, an opening for introducing a sample liquid is not shielded by the shield. Thus, there has been a problem that the influence of noise from such a portion cannot be avoided.

Figure 1:
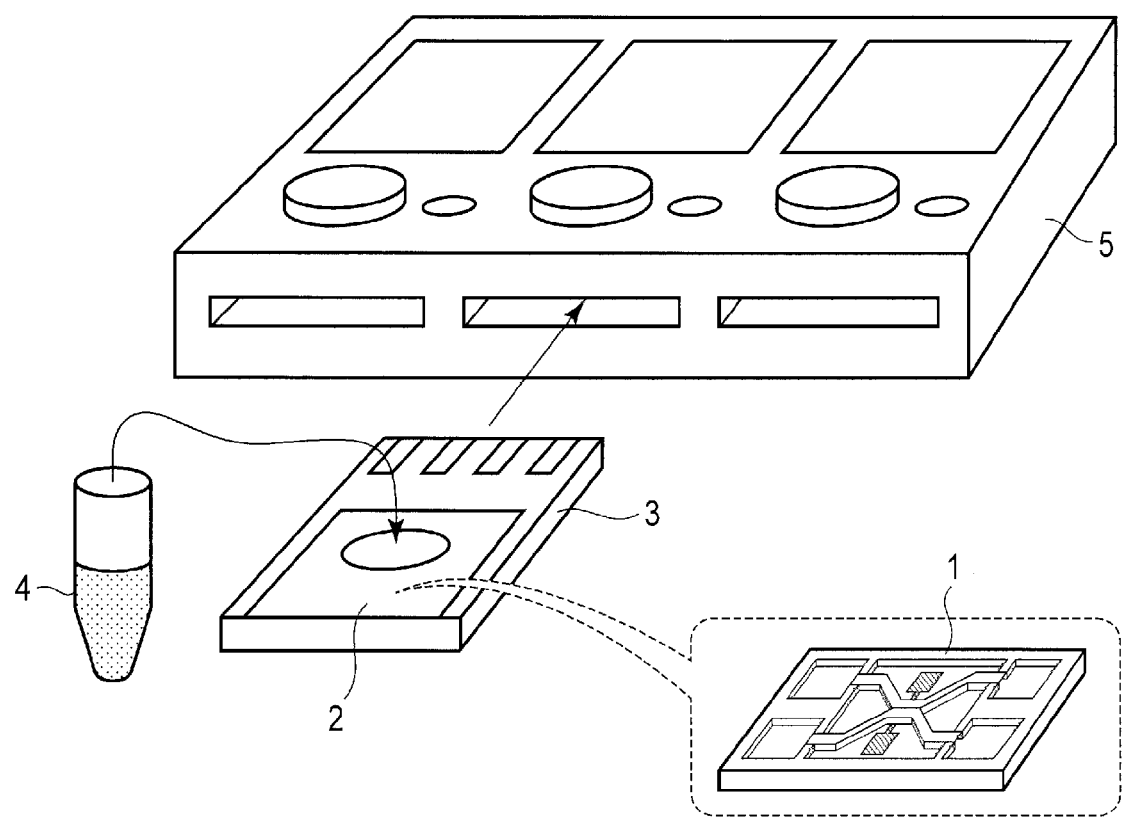
FIG. 1 is a perspective view showing a structure example of a microanalysis system.

FIG. 1 is for explaining a first embodiment, and is a perspective view showing a structure example of a microanalysis system.

An analysis chip, for instance, a semiconductor microanalysis chip 1 does not function alone, and is mounted on a circuit board (board comprising a wiring layer) with a detection IC. In addition, the semiconductor microanalysis chip 1 and the detection IC are molded from resin, etc. A package formed by resin molding is used as a microanalysis package 2.

The microanalysis package 2 is generally set in a cassette 3 when being used. In addition, the microanalysis package 2 is provided for a test of particles by inserting the cassette 3 into a determination device 5 after dropping a sample liquid 4 onto a necessary portion of the chip 1.

Figure 2:
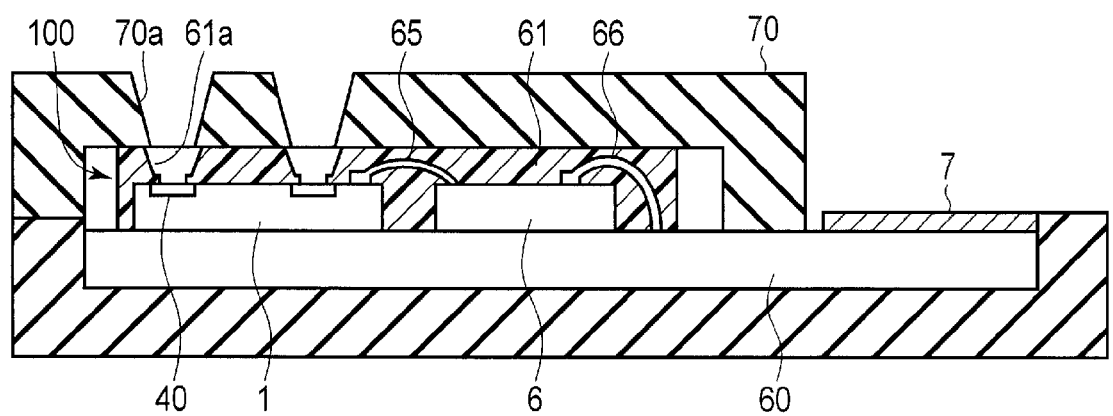
FIG. 2 is a cross-sectional view showing a basic structure of a microanalysis package used in the microanalysis system of FIG. 1.

FIG. 2 is a cross-sectional view showing an example of a basic structure of the microanalysis package 2.

The semiconductor microanalysis chip 1 and an IC 6 for current-voltage conversion are mounted on a circuit board 60. The semiconductor microanalysis chip 1 and the IC 6 are electrically connected by a bonding wire 65, and the IC 6 is electrically connected to the circuit board 60 by a bonding wire 66. In addition, an external electrical connection terminal (electrical signal input/output terminal) 7 is provided on the circuit board 60.

A mold layer 61 is formed on the circuit board 60 on which the semiconductor microanalysis chip 1 and the IC 6 are mounted to cover the semiconductor microanalysis chip 1 and the IC 6. The mold layer 61 is, for example, an epoxy resin, and comprises openings 61a above reservoirs 40 which are flow channel openings of the semiconductor microanalysis chip 1. Here, a package obtained by packaging the semiconductor microanalysis chip 1 and the IC 6 in the mold layer 61 is the microanalysis package 2.

The microanalysis package 2 is accommodated in a housing 70 which surrounds the microanalysis package 2. Openings 70a connected to the openings 61a of the mold layer 61 are provided at parts of the housing 70. In addition, a connection terminal 7 provided on the circuit board 60 is exposed to the outside of the housing 70.

Figure 3:
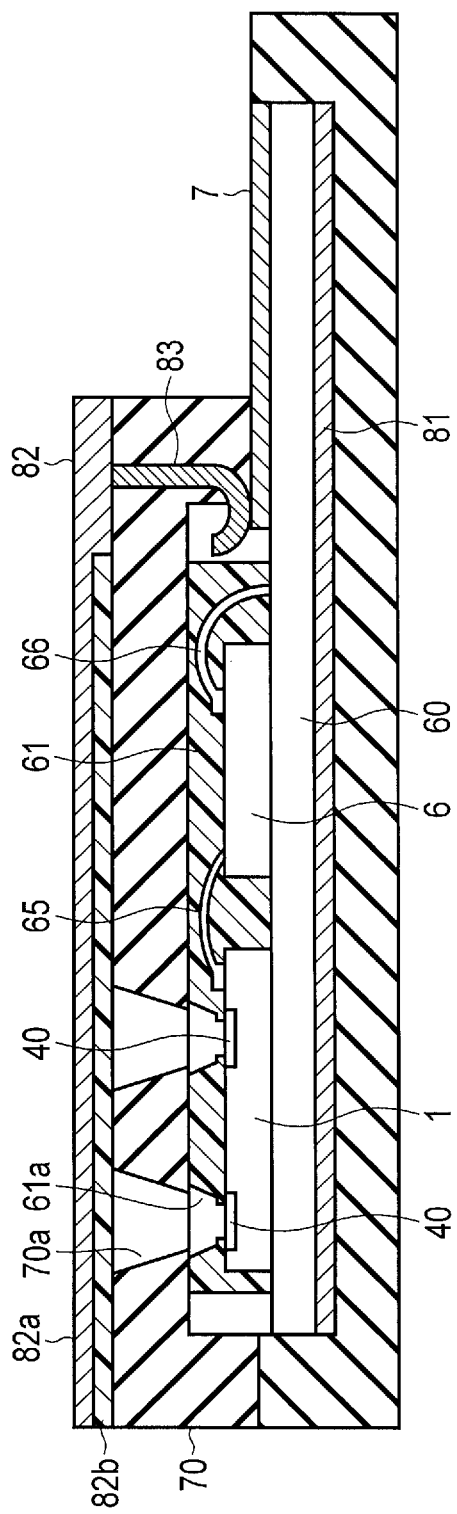
FIG. 3 is a cross-sectional view showing a schematic structure of a microanalysis package according to a first embodiment.

In addition, in the present embodiment, a shield structure is added to remove the influence of external noise. FIG. 3 is a cross-sectional view showing a schematic structure of a microanalysis package according to the first embodiment.

In the structure of FIG. 3, a first shield layer 81 is provided on a back surface of the circuit board 60 in addition to the structure of the FIG. 2. Moreover, a second shield layer 82 composed of an electrically conductive sheet is provided on a top surface of the housing 70 to be attachable and detachable.

The first shield layer 81 is a metal film of Al, W, Cu, Ni, Au, etc., and it suffices that the first shield layer 81 is formed on the back surface of the circuit board 60 by vapor deposition, sputtering or plating, etc. The first shield layer 81 is connected to a part of an earth terminal (not shown in the figure) or the connection terminal 7 of the housing 70.

The second shield layer 82 is a metal foil seal obtained by forming a metal film on a base material such as a resin and forming an adhesive on its back surface. In addition, a metal film portion 82a is electrically connected to the connection terminal 7, and a resin portion 82b is attachable and detachable. That is, a part of the metal film portion 82a is fixed to an outer wall surface of the housing 70, and is connected to a part of the connection terminal 7 through an interconnect 83 penetrating the housing 70. The resin portion 82b doubles as an adhesive layer, and is attachable to and detachable from the outer wall surface of the housing 70.

In the second shield layer 82, the resin portion 82b is peeled off from the housing 70 when a sample liquid is injected, and is reattached at the time of measurement. This prevents a hole in an electrical shield from opening at portions of the sample liquid injection holes (openings 70a). Moreover, because the openings 70a can be closed by the resin portion 82b at the time of disposal, contamination can be prevented.

Figure 4:
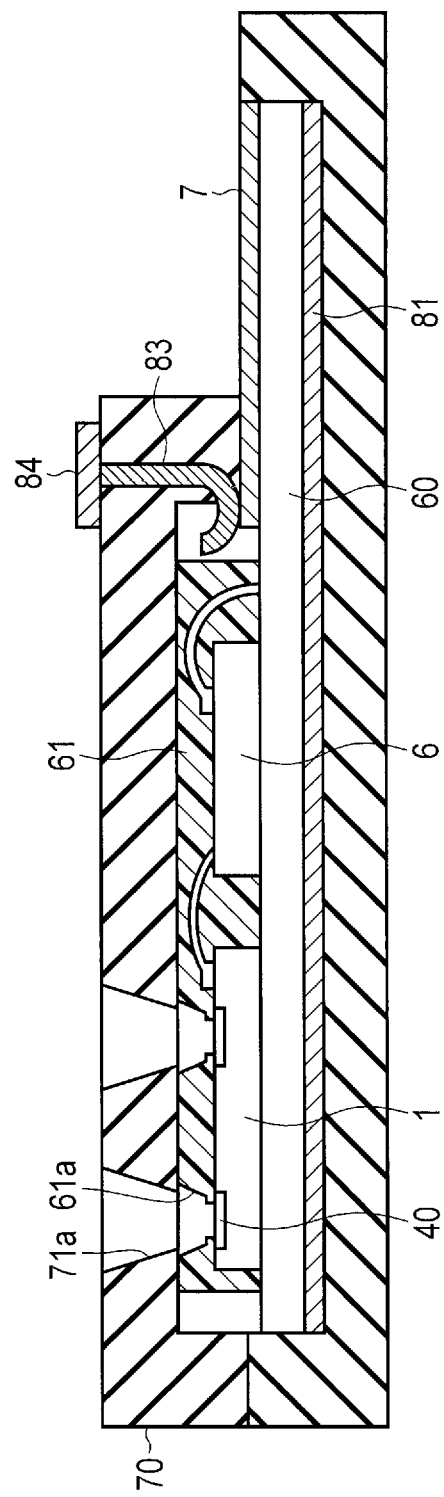
FIG. 4 is a cross-sectional view showing a modification of the microanalysis package according to the first embodiment.

It should be noted that the second shield layer 82 makes a component set with a package, and may be attached after a sample liquid is injected. At this time, it suffices that an electrode 84 connected to the connection terminal 7 is exposed to the top surface of the housing 70 as shown in FIG. 4, and then, the metal film portion 82a and the electrode 84 are surely connected when the second shield layer 82 is attached.

In this manner, in the present embodiment, the first shield layer 81 and the second shield layer 82 are provided on the back surface of the circuit board 60 and on the outer wall surface of the housing 70, respectively, with the microanalysis package 2 interposed therebetween. The microanalysis package can be thereby shielded. In addition, since a metal foil seal is used as the second shield layer 82 in this case, the resin portion 82b is peeled off when a sample liquid is injected, and is reattached at the time of measurement, whereby a hole in an electrical shield does not open at the sample liquid injection holes. Thus, the openings for sample liquid introduction are also surely shielded, whereby device reliability can be improved.

Furthermore, the openings 70a of the housing 70 can be closed by the second shield layer 82 when the microanalysis package is disposed of. Therefore, contamination due to viruses, etc., in the microanalysis package can be prevented.

(Second Embodiment)

Figure 5:
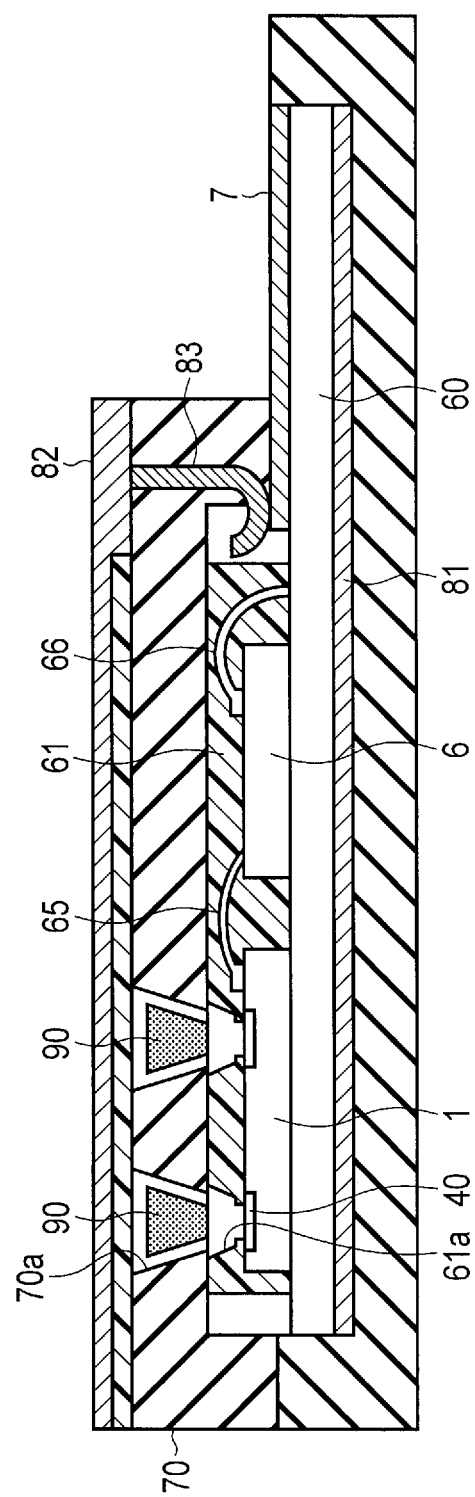
FIG. 5 is a cross-sectional view showing a schematic structure of a microanalysis package according to a second embodiment.

FIG. 5 is a cross-sectional view showing a schematic structure of a microanalysis package according to a second embodiment. It should be noted that the same portions as those of FIG. 3 are given the same numbers as those of FIG. 3, and detailed explanations thereof will be omitted.

In the present embodiment, in addition to the structure of the above-described first embodiment, liquid immersion fibers 90 immersed in a liquid such as alcohol and water are provided in openings 70a of a housing 70. As the liquid immersion fibers 90, for example, a nonwoven fabric of a synthetic fiber such as rayon or polyester which is immersed in ethanol, etc., can be used.

In the above-described structure, since the liquid immersion fibers 90 are provided in the openings 70a of the housing 70, the surface state of flow channel walls of a semiconductor microanalysis chip 1 can be prevented beforehand from being hydrophobic because of change over time. Thus, the same advantages as those of the first embodiment can be obtained as a matter of course, and moreover, reliability can be further improved. In addition, since a second shield layer 82 is provided, there is also an advantage that the liquid immersion fibers 90 can be prevented from dropping from the openings 70a.

(Third Embodiment)

As a third embodiment, various examples of a semiconductor microanalysis chip used in the first and second embodiments are first described with reference to FIG. 6A, FIG. 6B, FIG. 7, and FIG. 8.

FIG. 6A and FIG. 6B are illustrations for explaining a schematic structure of a first semiconductor microanalysis chip. FIG. 6A is a plan view, and FIG. 6B is a cross-sectional view taken along line A-A' of FIG. 6A. Here, the uppermost surface in FIG. 6A is shown with a cap layer 18 in FIG. 6B removed.

In this semiconductor microanalysis chip, an insulating film 15, an insulating film 17, and the insulating film 18 are formed in lamination on a semiconductor substrate 10. As the semiconductor substrate 10, for example, Si is used, but other substrates which can be processed in the same way as Si, for example, Ge and SiC, can also be used. In addition, as the insulating films 15, 17, and 18, a dielectric film of $SiO_2$, $Si_3N_4$, $Al_2O_3$, etc., and a polymer material such as polyimide can be used. A first microflow channel 21 is formed by excavating a surface of the Si substrate 10 to a depth of, for example, 2 µm, and one end side of the flow channel 21 is connected to an introduction opening 45 of a sample liquid. On the introduction opening 45 side of the first flow channel 21, a column (pillar) array 50 extending from a bottom surface of the flow channel to a top surface of the flow channel is formed.

The insulating film 15 is formed to cover the first flow channel 21, and in a part thereof, a microaperture 30 is formed. In the insulating film 17, the introduction opening 45, an ejection opening 46, and a second microflow channel 22 are formed. The insulating film 18 is formed to cover the second microflow channel 22, and in parts thereof, the introduction opening 45 and the ejection opening 46 are formed. The microaperture 30 communicates from the top surface of the first microflow channel 21 to a bottom surface of the second microflow channel 22, and the first microflow channel 21 and the second microflow channel 22 are spatially connected through the microaperture 30.

The opening size of the microaperture 30 is slightly larger than a particle to be detected (the maximum diameter of a virus, bacterium, pollen grain, or a compound thereof with other particles). More specifically, the opening size of the microaperture 30 is larger than the outer diameter of a particle to be detected by 5% or more, and is a size which allows a particle to pass through the microaperture by liquid pressure or electrophoresis. In addition, it suffices that the opening size of the microaperture 30 is determined in consideration of how easily a particle to be detected pass therethrough and the sensitivity to change in ion current, which will be described later, and is, for example, 1.5 to 5 times the outer diameter of a particle to be detected.

In the semiconductor microanalysis chip having the above-described structure, when a sample liquid (liquid including particles to be detected) is injected into the introduction opening 45, the sample liquid flows into the first microflow channel 21 by capillarity effect, and reaches the microaperture 30. As a liquid including particles (specimens) to be detected, a liquid which can be electrified, for example, an electrolytic solution such as a KCl aqueous solution, and various buffer solutions such as a tri ethylene diamine tetra acetic acid (TE) buffer solution and a phosphate buffered saline (PBS) buffer solution, can be used. Then, the second microflow channel 22 is filled with a liquid which can be electrified and does not include sample particles. Particles in a sample liquid move in the flow channel, following the inflow of a sample liquid of the first microflow channel 21 because of capillarity. In this state, electrodes such as metal wires may be inserted into the introduction opening 45 and the ejection opening 46, respectively, as necessary to force sample particles to electrophoretically move by applying a voltage between the electrodes.

Next, electrodes (metal wires, etc.) for observing a current passing through the microaperture 30 are inserted into the introduction opening 45 and the ejection opening 46, respectively, and a voltage is applied to observe an ion current flowing therebetween. When particles are moved by an electric field and pass through the microaperture 30, an opening of the microaperture 30 is shielded if the particles are insulative. Thus, the electrical resistance of an ion current path increases, and an ion current decreases. In contrast, if the particles are electrically conductive and have electron affinity by which a potential barrier with a sample liquid is hardly formed, an increase in ion current may be observed. By observing this change in ion current, it can be detected that the particles have passed through the microaperture 30.

The pillar array 50 extending from the bottom surface of the flow channel to the top surface of the flow channel is disposed in the first microflow channel 21 at appropriate pillar intervals, whereby unnecessary particles large in size are trapped and only particles small in size are allowed to pass downstream. For example, to detect a virus approximately 100 nm in size, a giant particle greater than or equal to 0.5 μm can be prevented from reaching and closing the microaperture 30 by setting the pillar intervals of the pillar array 50 at 250 nm. In addition, the maximum sizes of particles reaching the microaperture 30 can be evened out by appropriately adjusting the pillar intervals and the array length of the pillar array 50. Moreover, because a peak current greater than or equal to a certain change in ion current to be detected can be calculated as a part of noise distribution, detection accuracy can be improved.

In addition, the pillar array 50 can also be formed in the second microflow channel 22 to prevent a dust back current from the ejection opening side, and moreover, a slitlike flow channel array, etc., can also be used instead of the pillar array 50.

Figure 7:
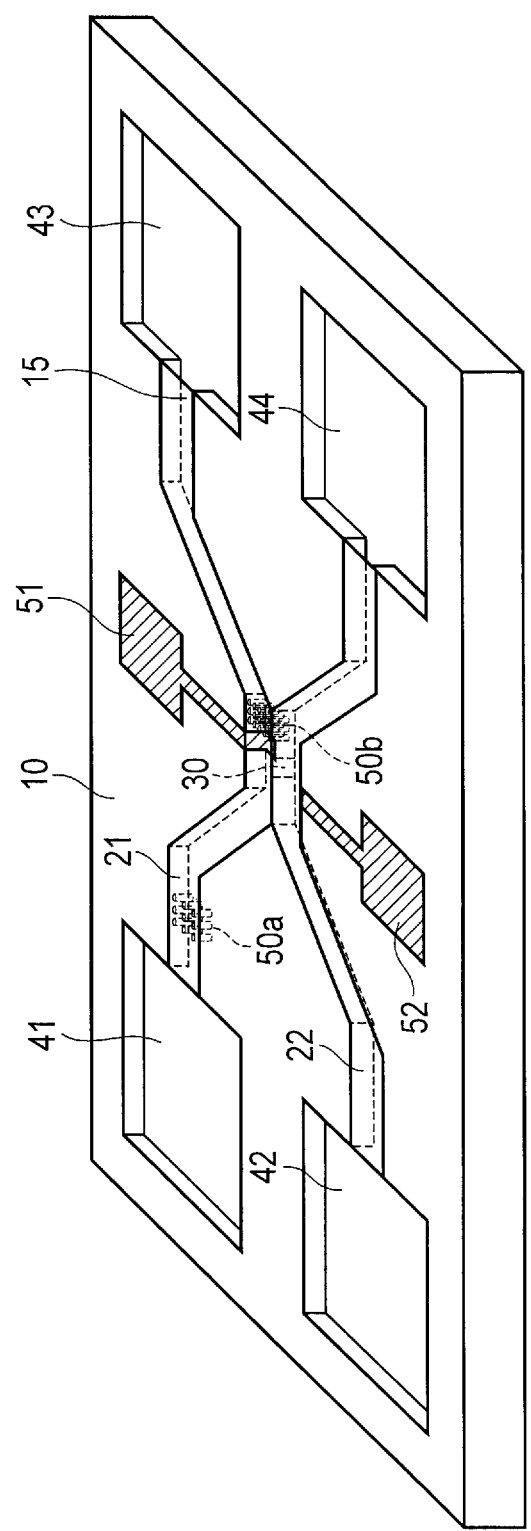
FIG. 7 is a perspective view showing an example of the semiconductor microanalysis chip used in the first and second embodiments.

FIG. 7 is a perspective view showing a schematic structure of a second semiconductor microanalysis chip.

10 in the figure denotes a semiconductor substrate, and as the substrate 10, various semiconductors such as Si, Ge, SiC, GaAs, InP, and GaN can be used.

41 to 44 denote reservoirs for injecting and ejecting a sample liquid: 41 denotes a sample liquid introduction region; 42 denotes an electrolyte solution introduction region; 43 denotes a sample liquid ejection region; and 44 denotes a second electrolyte solution ejection region. These reservoirs 41 to 44 are formed by excavating a surface portion of the Si substrate 10 to a depth of 2 μm, for example, in a pattern of a square with 1 mm sides, for example, by selective etching.

21 denotes a first microflow channel for letting a sample liquid flow, and 22 denotes a second microflow channel for letting an electrolyte solution flow. These microflow channels 21 and 22 are disposed in different layouts, such that parts thereof are close to each other. For example, the microflow channels 21 and 22 are formed by excavating the Si substrate 10 to a width of 50 μm and a depth of 2 μm. Moreover, top portions of the microflow channels 21 and 22 are covered by an insulating thin film (for example, having a thickness of 200 nm) such as a silicon oxide film ($SiO_2$), a silicon nitride film (SiNx), and an alumina film ($Al_2O_3$). That is, a cap layer 15 (lid sealing the flow channels) is formed. Thus, both the first and second microflow channels are trench type tunnel flow channels.

At this time, the cap layer 15 is basically formed toward joints between the top portions of the reservoirs 41 to 44 and the flow channels. However, the flow channel cap is not formed on at least parts of the joints between the top portions of the reservoirs 41 to 44 and the flow channels to allow a sample liquid or an electrolyte solution to pass therethrough. Thus, the microflow channels 21 and 22 are tunnel flow channels opening at reservoir portions.

30 denotes a microaperture provided at a contact portion between the first microflow channel 21 and the second microflow channel 22, and is formed by removing a part of a partition 31 (for example, $SiO_2$ having a thickness of 2 μm) between the flow channel 21 and the flow channel 22 by etching in a slit. The size (width) of the microaperture 30 is slightly greater than the size of a particle to be detected, and if the size of a particle to be detected is 1 μmφ, the width of the microaperture 30 is, for example, 1.5 μm.

51 and 52 denote electrodes for detecting particles, and are formed to be exposed to insides of the microflow channels 21 and 22, respectively. As materials for these electrodes, it suffices that surfaces contacting a sample liquid are made of AgCl, Pt, Au, Cu, W, or the like. In addition, the electrodes may not necessarily be integrated as shown in FIG. 7, and particles can also be detected by inserting external electrodes into the reservoirs of the respective flow channels.

An ion current passing through the microaperture 30, that is, a current which flows when the two microflow channels 21 and 22 are filled with an electrolyte solution (solution in which an ion current can flow when an electrolyte is dissolved) and a voltage is applied to the electrodes 51 and 52 (steady-state current which flows when particles are not passing), is basically determined on the basis of the opening size of the microaperture 30. In addition, when particles to be detected pass through the microaperture 30, the particles close a part of the microaperture 30 and block the passage of an ion, and a current decreases accordingly. However, if particles are electrically conductive or can conduct a surface level, the particles receive an ionic charge, and a current may increase because of electrical conduction of the particles themselves. Because this change in ion current is determined on the basis of the relationship between the shapes, the sizes, the lengths, etc., of the microaperture 30 and the particles, the substance of particles passing through the microaperture can be calculated by observing the amount of change, change over time, etc., in ion current.

It suffices that the opening size of the microaperture 30 is determined in consideration of how easily a particle to be detected pass therethrough and the degree of change (sensitivity) in ion current, and is, for example, 1.5 to 5 times the outer diameter of a particle to be detected. In addition, as an electrolyte solution in which particles to be detected are dispersed, for example, an electrolytic solution such as a KCl aqueous solution, and various buffer solutions such as a tri ethylene diamine tetra acetic acid (TE) buffer solution and a phosphate buffered saline (PBS) buffer solution, can be used.

In the semiconductor microanalysis chip like this, particles can be detected only by introduction of a sample liquid and electrical observation. Moreover, the semiconductor microanalysis chip can be microminiaturized and produced on a large scale by semiconductor processing technology, and a particle detection circuit, a discrimination/determination circuit, etc., can be integrated. Thus, a microminiature and supersensitive microanalysis chip can be produced on a large scale at small cost. Accordingly, supersensitive detection of bacteria and viruses can be easily performed, and a contribution can be made to the field of preventing the spread of epidemic diseases and ensuring the safety of food, etc., by application to simple detection of epidemic pathogens and causative bacteria of food poisoning, etc. Such semiconductor microanalysis chips are suitable for uses in the case where a huge amount needs to be provided at extremely small cost, for example, uses for high-speed primary test kits for diseases which need to be dealt with by emergency quarantine, such as a new type of influenza, and simple food poisoning tests in ordinary households.

50a and 50b in the figure denote pillar arrays in microsize which comprise microcolumns (pillars) arranged at regular intervals, and filter particles in a sample liquid according to size through the intervals. As the pillar arrays 50a and 50b, wall (slit) arrays can also be used.

Figure 8:
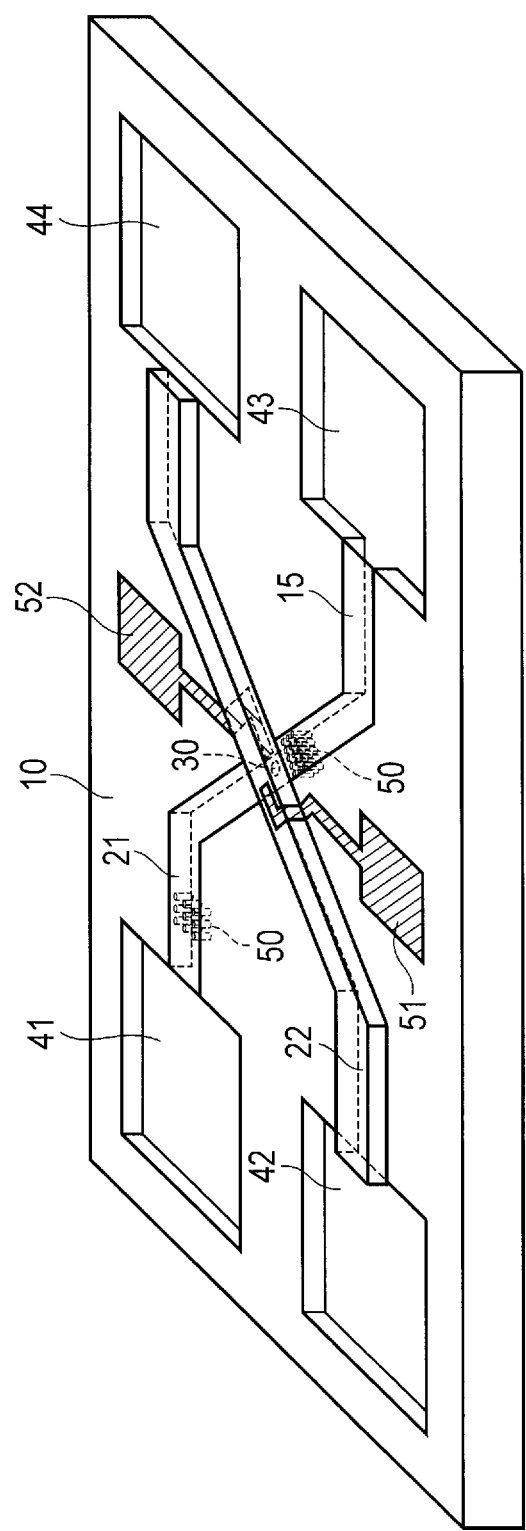
FIG. 8 is a perspective view showing an example of the semiconductor microanalysis chip used in the first and second embodiments.

FIG. 8 is a plan view showing a schematic structure of a third semiconductor microanalysis chip, and shows an example of forming microflow channels 21 and microflow channel 22 in different processes and providing a stack portion (contact portion) at which the two microflow channels 21 and 22 intersect. Here, the flow channels are formed in two stages in which the flow channel 21 to be a sample introduction flow channel is formed on the lower side and the flow channel 22 to be a sample reception flow channel is formed on the upper side. At this time, a microaperture 30 is provided at the stack portion (contact portion) of the two flow channels, and is formed on a partition (cap insulating film of the first flow channel) which is a top surface of the first microflow channel 21 and is a bottom surface of the second microflow channel 22 by photolithography.

In the semiconductor microanalysis chip of FIG. 7, the two microflow channels 21 and 22 are adjacent in a lateral direction with the partition interposed therebetween, the microaperture 30 needs to be formed on the partition vertical to a Si substrate 10, and the slitlike microaperture 30 is formed by patterning a side of the partition. The shape of the microaperture at this time is a quadrangle close to a square if the depth of the flow channels and the width of the microaperture are the same, and is an oblong slit if the depth of the flow channels is greater than the width of the microaperture. Therefore, there has been a problem that when particles pass through the microaperture 30, the opening of the microaperture 30 cannot be sufficiently shielded by the particles, and the change in ion current is less than in the case where the microaperture is circular.

On the other hand, in the semiconductor microanalysis chip of FIG. 8, since the microaperture 30 can be directly patterned and the opening shape of the microaperture 30 can be arbitrarily formed, a circular opening which can shield ionic conduction by particles the most efficiently can be formed. The change in ion current when particles to be detected pass through the microaperture 30 can thereby be maximized, and particles can be detected with higher sensitivity than in the second microanalysis chip.

The first microflow channel 21 is a tunnel flow channel of an excavation type, and the second microflow channel 22 is a flow channel of an insulating film tunnel type. In addition, at the contact portion at which the two flow channels 21 and 22 intersect, the microaperture 30 is formed in the insulating film 15, and the opening shape thereof can be arbitrarily formed. Electrodes which observe an ion current are formed on the bottom surface of the first microflow channel 21 and the top surface of the second microflow channel 22. Higher sensitivity through optimization of the shape of the microaperture can thereby be achieved.

It should be noted that since the two flow channels 21 and 22 are herein disposed to intersect, a sample liquid dropped into a reservoir 41 is ejected to a reservoir 43. As a matter of course, the two flow channels 21 and 22 may also be disposed to turn toward the reservoirs 44 and 43, respectively, at the portion where the two flow channels 21 and 22 stack and contact each other (in this case, a sample liquid dropped into the reservoir 41 is ejected to the reservoir 44).

In the semiconductor microanalysis chip like this, since the two microflow channels 21 and 22 intersect, the microaperture 30 can have a circular opening. Particles can thereby be detected with higher sensitivity.

(Modification)

It should be noted that the present invention is not limited to each of the above-described embodiments.

The structure of a microanalysis chip is in no way limited to those shown in FIG. 6A, FIG. 6B, FIG. 7, and FIG. 8. It suffices that a detector for detecting a particle, a flow channel for injecting and ejecting a sample liquid for particle detection to the detector, and a liquid receiver for introducing the sample liquid into the flow channel from outside are provided. Moreover, a substrate on which the microanalysis chip is formed is not necessarily limited to a semiconductor substrate, and may be, for example, a material such as quartz obtained by oxidizing the whole semiconductor. In other words, the substrate may be any substrate in which a microflow channel and a microaperture for particle detection can be formed.

If a microanalysis package can have sufficient strength only by a mold, a housing accommodating the package is not necessarily needed, and can also be omitted. Moreover, the microanalysis package need not necessarily be set in a cassette when being used, and can also be used in a package alone.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analysis package for detecting particles in a sample liquid, comprising:
   a board comprising an electrical input/output terminal;
   an analysis chip provided at a part of the board, the chip comprising a detector for detecting a particle, a flow channel for injecting and ejecting the sample liquid for particle detection to the detector, and a liquid receiver for introducing the sample liquid into the flow channel;

a mold provided to cover the board on which the analysis chip is provided, the mold comprising an opening above the liquid receiver;
a first electro-magnetic shield layer provided on a back surface of the board; and
a second electro-magnetic shield layer provided to cover an opposite side to the analysis chip of the mold and to be attachable and detachable on the opposite side to the analysis chip of the mold, the second electro-magnetic shield layer being electrically connected to a part of the electrical input/output terminal in a state of being attached to the opposite side to the analysis chip of the mold.

2. The package of claim 1, further comprising a housing accommodating the board, the analysis chip, and the mold, wherein the second shield layer is provided on an outer wall surface of the housing.

3. The package of claim 1, wherein the second shield layer is an electrically conductive thin film tape.

4. The package of claim 1, further comprising a liquid immersion fiber provided in the opening of the mold, the liquid immersion fiber being immersed in a liquid.

5. The package of claim 1, wherein the flow channel comprises first and second flow channels which overlap or intersect with each other, and a microaperture as the detector is formed at an overlap or an intersection of the first and second flow channels.

6. The package of claim 1, further comprising a semiconductor device for detection provided on the board for converting a detection result of the detector into an electrical signal.

7. The package of claim 6, wherein the semiconductor device for detection, with the analysis chip, is covered by the mold.

8. The package of claim 1, further comprising pillars provided in the flow channel.

9. An analysis package comprising:
a board comprising an electrical input/output terminal;
an analysis chip provided on the board, the chip comprising a detector for detecting a particle, a flow channel for injecting and ejecting a sample liquid for particle detection to the detector, and a liquid receiver for introducing the sample liquid into the flow channel;
a mold provided on the board on which the analysis chip is provided, the mold comprising an opening above the liquid receiver;
a first shield layer provided on a back surface of the board;
an electrode provided to be exposed on an opposite side to the analysis chip of the mold, the electrode being electrically connected to a part of the electrical input/output terminal; and
a second shield layer which is configured to be attachable and detachable on the opposite side to the analysis chip of the mold and is electrically connected to the electrode in a state of being attached to the opposite side to the analysis chip of the mold.

10. The package of claim 9, further comprising a housing accommodating the board, the analysis chip, and the mold, wherein the electrode is provided on an outer wall surface of the housing.

11. The package of claim 9, wherein the second shield layer is an electrically conductive thin film tape.

12. The package of claim 9, further comprising a liquid immersion fiber provided in the opening of the mold, the liquid immersion fiber being immersed in a liquid.

13. The package of claim 9, wherein the flow channel comprises first and second flow channels which overlap or intersect with each other, and a microaperture as the detector is formed at an overlap or an intersection of the first and second flow channels.

14. The package of claim 9, further comprising a semiconductor device for detection provided on the board for converting a detection result of the detector into an electrical signal.

15. The package of claim 14, wherein the semiconductor device for detection, with the analysis chip, is covered by the mold.

16. The package of claim 9, further comprising pillars provided in the flow channel.

* * * * *